United States Patent [19]

Thorogood

[11] 4,328,234
[45] May 4, 1982

[54] IMIDAZOLE DERIVATIVES AND SALTS THEREOF AND PHARMACEUTICAL FORMULATIONS USEFUL IN THROMBO-EMBOLIC DISORDERS

[75] Inventor: Peter B. Thorogood, London, England

[73] Assignee: Burroughs Wellcome Co., Research Triangle Park, N.C.

[21] Appl. No.: 123,712

[22] Filed: Feb. 21, 1980

[30] Foreign Application Priority Data

Feb. 22, 1979 [GB] United Kingdom ............... 06243/79

[51] Int. Cl.³ .................. A61K 31/46; A61K 31/445; A61K 31/415; C07D 451/02
[52] U.S. Cl. .................................... 424/265; 424/267; 424/273 R; 546/16; 546/94; 546/125; 546/133; 548/335; 548/336; 548/337; 548/341; 548/342; 548/347; 548/348
[58] Field of Search ...................... 548/336, 335, 341; 546/133, 94, 16, 125; 424/273 R, 267, 265

[56] References Cited

U.S. PATENT DOCUMENTS

| | | | |
|---|---|---|---|
| 2,836,598 | 5/1958 | Archer | 546/125 |
| 3,401,168 | 9/1968 | Wasson et al. | 548/336 X |
| 3,666,755 | 5/1972 | Wagner et al. | 548/341 X |
| 3,682,951 | 8/1972 | Kreider | 548/341 |
| 3,769,422 | 10/1973 | Timmler et al. | 548/335 X |
| 4,031,224 | 6/1977 | Martin et al. | 548/336 X |
| 4,036,975 | 7/1977 | Walker et al. | 548/341 X |
| 4,057,549 | 11/1977 | Adelstein et al. | 548/336 X |
| 4,107,206 | 8/1978 | Hewett et al. | 548/341 X |
| 4,156,694 | 5/1979 | Hewett et al. | 548/335 X |

FOREIGN PATENT DOCUMENTS

719664 2/1969 Belgium .

OTHER PUBLICATIONS

Iwasaki, S., Helv. Chim. Acta, 59(8), 2753–2764 (1976).
Iwasaki, S., Helv. Chim. Acta, 61(8), 2831–2842 (1978).
Chemical Abstracts, 83:179065p (1975), [German OLS 2,363,014, Narr et al., 7/17/75].
Chemical Abstracts, 72:121067x (1970), [Dikolenko et al., *Vestn. Kiev. Politekm. Inst. Ser. Khim. Mashinostr. Tekhnol.* 1968(5), 166–169].

*Primary Examiner*—Richard A. Schwartz
*Attorney, Agent, or Firm*—Donald Brown

[57] ABSTRACT

Imidazoles of formula (I)

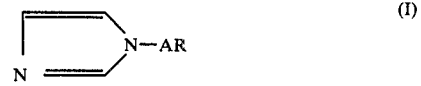

wherein
A is a chemical bond or a straight or branched, saturated or unsaturated, aliphatic residue having from 1 to 6 carbon atoms wherein 1, 2 or 3 of such carbon atoms may be replaced by a corresponding number of heteroatoms selected from oxygen, sulphur and nitrogen providing (in the case of 2 or 3 heteroatoms) that any such heteroatom is not located adjacent to a further such heteroatoms or heteroatoms R is a fused, saturated or unsaturated, non-aromatic carbocyclic, polycyclic ring system; a saturated or unsaturated, carbocyclic spirocyclic ring system, optionally containing one or more ring heteroatoms selected from oxygen, sulphur and nitrogen; or a saturated or unsaturated, carbocyclic bridged-polycyclic ring system, optionally containing one or more ring heteroatoms selected from oxygen, sulphur and nitrogen and having one or more bridges;

or AR together represent a straight or branched, saturated or unsaturated, aliphatic residue having 3 to 6 carbon atoms, wherein 1, 2 or 3 of such carbon atoms may be replaced by a corresponding number of heteroatoms selected from oxygen, sulphur and nitrogen providing (in the case of 2 or 3 heteroatoms) that any such heteroatom is not located adjacent to a further such heteroatom or heteroatoms; which aliphatic residue is substituted by at least two groups, which may be the same or different, selected from the groups specified for R above.

and acid addition salts and pharmaceutically acceptable bioprecursors thereof.

Methods of preparing the imidazoles are disclosed.

The imidazoles and their acid addition salts and bioprecursors are useful in the treatment or prophylaxis of thrombo-embolic conditions.

6 Claims, No Drawings

IMIDAZOLE DERIVATIVES AND SALTS THEREOF AND PHARMACEUTICAL FORMULATIONS USEFUL IN THROMBO-EMBOLIC DISORDERS

The present invention relates to imidazole derivatives and salts thereof, to their synthesis, to pharmaceutical formulations containing such compounds and to the use of these compounds in medicine.

Thromboxane $A_2$ ($TXA_2$), a potent stimulator of blood platelet aggregation, is produced in platelets, from the prostaglandin endoperoxides $PGG_2$ and $PGH_2$. Prostacyclin ($PGT_2$), which has potent anti-aggregatory activity, is also produced (in blood vessel walls) from $PGG_2$ and $PGH_2$ and it has been suggested that a balance between the production of $TXA_2$ and $PGT_2$ is the controlling factor in thrombus formation. It would, in consequence, be desirable in the treatment or prophylaxis of thrombo-embolic disorders to be able to selectively inhibit $TXA_2$ synthetase, thereby favouring the production of the anti-aggregatory agent $PGI_2$.

Imidazole and 1-methylimidazole are known to provide some degree of inhibition of the enzymic conversion of the endoperoxides ($PGG_2$ and $PGH_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Pat. No. 1 364 312; Biochem. Pharmacol., 24, 1902–1903, 1975).

We have now discovered that $TXA_2$ synthetase may be inhibited by 1-substituted imidazoles of formula (I), and acid addition salts thereof. The compounds of formula (I), and their salts, are hereinafter referred to as the "active compounds".

Compounds of formula (I) are imidazoles:

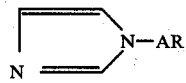

(I)

wherein

A is a chemical bond or a straight or branched, saturated or unsaturated, aliphatic residue having from 1 to 6 carbon atoms, optionally substituted and/or optionally including 1, 2 or 3 heteroatoms selected from oxygen, sulphur and nitrogen providing (in the case of 2 or 3 heteroatoms) that any such heteroatom is not located adjacent to a further such heteroatom or heteroatoms, the total number of said carbon atoms and heteroatoms not exceeding 6.

R is a fused, saturated or unsaturated, non-aromatic carbocyclic, bi- or tri-cyclic ring system providing that when R is a 9-decahydronaphthyl group, A does not represent a carbonyl group; a saturated or unsaturated, carbocyclic spirocyclic ring system, optionally containing one or more ring heteroatoms selected from oxygen, sulphur and nitrogen; or a saturated or unsaturated, carbocyclic bridged-polycyclic ring system, optionally containing one or more ring heteroatoms selected from oxygen, sulphur and nitrogen and having one or more bridges providing that when R is an adamantanyl group, A does not represent an ethylene radical (—$(CH_2)_2$—) substituted at the carbon atom α to the adamantanyl group by a hydroxy, oxo, ether or thioether grouping;

or AR together represent a straight or branched, saturated or unsaturated, aliphatic residue having 3 to 6 carbon atoms, optionally substituted and/or optionally including 1, 2 or 3 heteroatoms selected from oxygen, sulphur and nitrogen providing (in the case of 2 or 3 heteroatoms) that any such heteroatom is not located adjacent to a further such heteroatom or heteroatoms, the total number of said carbon and heteratoms not exceeding 6; which aliphatic residue is substituted by at least two groups, which may be the same or different, selected from the groups specified for R above.

Acid addition salts of compounds of formula (I) are preferably pharmaceutically acceptable salts of such compounds.

The present invention also includes within its scope pharmaceutically acceptable bioprecursors (otherwise known as pro-drugs) of the compounds of formula (I), i.e. compounds which have a different formula to formula (I) above but which nevertheless upon administration to an animal or human being are converted directly or indirectly in vivo into a compound of formula (I).

When the compounds of formula (I) contain an asymmetric centre, the present invention includes the optically active stereoisomers as well as racemic mixtures thereof. If desired, the optically active stereoisomers may be resolved in conventional manner, e.g. by fractional crystallisation.

The group A preferaby contains 1, 2 or 3 carbon atoms, and most preferably is a methylene (—$CH_2$—) or ethylene (—$(CH_2)_2$—) radical.

Although the group A is preferably a hydrocarbon group, it may carry one or more non-hydrocarbon substituents, e.g. trifluoromethyl or hydroxyl substituents, and may include an oxo group.

The above-mentioned spiro and bridged polycyclic groups R are preferably carbocyclic groups, but they may include, if desired, one or more heteroatoms selected from oxygen, sulphur and nitrogen, preferably not more than 2 such heteroatoms in each ring. Examples of groups in which R is a spirocyclic group are spiro[3,3]heptan-2-yl, spiro[3,4]octan-2-yl, spirobicyclohexan-4-yl, and cyclohexanespirocyclopentan-4-yl.

The term 'bridged polycyclic ring system' is used herein to denote a polycyclic system which includes two adjacent rings having at least three atoms in common.

It should be appreciated that the group R may comprise a combination of a bridged ring system (as defined above) and a fused ring system, as exemplified by the tricyclo[3.2.1.0$^{2,4}$]octan-6-yl radical.

The group R in general preferably contains up to 20 carbon atoms, advantageously up to 15 carbon atoms and particularly up to 10 carbon atoms.

When R is a bridged polycyclic radical, preferred bicyclo radicals include bicyclo[3.1.1]heptanyl particularly a 6,6-dimethylbicyclo[3.1.1]heptanyl radical such as 6,6-dimethylbicyclo[3.1.1]heptan-2-yl. Preferred bridged tricyclo radicals include adamantanyl particularly adamantan-1-yl.

Examples of other groups in which R is a bridged-polycyclic radical are bicyclo radicals such as bicyclo[2.2.1]heptan-1-yl, 3,3-dimethylbicyclo[2.2.1]heptan-2-ylidene, bornan-2-yl, pinan-3-yl, and 3,3-dimethylnorbornan-2-yl; and tricyclo radicals such as tricyclo[1.1.0.0$^{2,4}$]butyl, tricyclo[4.2.1.2$^{7,9}$]undecan-2-yl, tricyclo[5.4.0.0$^{2,9}$]undecan-4-yl, tricyclo[4.4.1.1$^{1,5}$]dodecan-3-yl, and tricyclo[4.1.0.0$^{2,4}$]heptan-3-yl.

When R is an unsaturated bridged polycyclic radical, preferred such radicals include bicyclo[3.1.1]heptenyl, particularly 6,6-dimethyl-bicyclo[3.1.1]heptenyl especially 6,6-dimethylbicyclo[3.1.1]-hept-2-en-2-yl.

Examples of other unsaturated R groups are spiro[4,5]deca-1,6-dien-9-yl; 2-cyclohexenespiro-2'-cyclopenten-3'-yl; 2-cyclohexanespirocyclobutan-3'-yl; 1-isopropylbicyclo[3.1.0]hex-3-en-2-yl, 5,7,7-trimethyl-norborn-5-en-2-yl, norborn-5-en-2-yl, 5-bornen-3-yl, bicyclo[2.2.2]oct-5-en-2-yl; tricyclo[3.2.1.0$^{2,7}$]oct-3-en-6-yl, tricyclo[3.2.1.0$^{2,6}$]oct-2-en-4-yl, and tricyclo[3.2.0.0$^{2,7}$]hept-3-en-6-yl.

Examples of an R group containing a heteroatom are cyclohexanespiro-2'-tetrahydrofuran-4'-yl, tetrahydropyran-2-spirocyclohexan-3'-yl, 1-azaspiro[2.5]octan-5-yl, and 7-azaspiro[3.5]nonan-2-yl.

Bicyclo examples of such groups are:
7-azabicyclo[2.2.1]heptan-2-yl,
4-azabicyclo[2.2.2]octan-2-yl,
8-methyl-8-azabicyclo[3.2.1]octan-3-yl, 3,6,8-trioxabicyclo[3.2.2]nonan-2-yl and
2,6-dioxabicyclo[3.2.1]octan-7-yl.

Tricyclic examples of such groups are:
2-azatricyclo[3.2.2.0$^{2,4}$]nonan-6-yl, and
3-azatricyclo[3.2.2.0$^{2,4}$]nonan-6-yl.

Unsaturated examples of such groups are:
3-azatricyclo[3.2.1.0$^{2,4}$]oct-6-en-6-yl,
9-oxatricyclo[4.2.1.0$^{2,5}$]non-7-en-3-yl, and
4,8,8-trimethyl-2-oxatricyclo[5.1.0.0$^{1,3}$]oct-4-en-6-yl.

Examples of groups in which R is a fused polycyclic radical include fused bicyclic or tricyclic radicals, for example 1- or 2-decahydronaphthyl, 1- or 2-decahydroazulenyl, or 1- or 2-octahydro-pentalenyl.

The group R may, if desired, be substituted by one or more substituents selected from hydroxy; halo, e.g. chloro, bromo, or fluoro; trihaloalkyl, e.g. trifluoromethyl; alkyl of from 1 to 3 carbon atoms, e.g. methyl; alkyloxy of from 1 to 3 carbon atoms, e.g. methoxy; carboxyl and esters thereof with alcohols of 1 to 3 carbon atoms.

Particularly preferred compounds of formula (I) are:
1-[2-(6,6-dimethylbicyclo[3.1.1]hept-2-en-2-yl)ethyl-]imidazole;
1-[2-(6,6-dimethylbicyclo[3.1.1]heptan-2-yl)ethyl-]imidazole;
1-(bicyclo[2.2.1]hept-5-en-2-ylmethyl)imidazole;
1-(bicyclo[2.2.1]heptan-2-ylmethyl)imidazole;
1-(6,6-dimethylbicyclo[3.1.1]heptan-2-ylmethyl)imidazole;
1-[2-(adamantan-1-yl)ethyl]imidazole,
1-(2-cyclohexenespirocyclobutan-3'-ylmethyl)imidazole,
1-(6,6-dimethylbicyclo[3.1.1]hept-2-en-2-ylmethyl)imidazole;
1-[2-(3,3-dimethylbicyclo[2.2.1]heptan-2-ylidene)ethyl]imidazole,
1-(4-azabicyclo[2.2.2]octan-2-ylmethyl)imidazole, 1-(8-methyl-8-azabicyclo[3.2.1]octan-3-ylmethyl)imidazole.

In contrast to imidazole and 1-methylimidazole the compound of formula (I) are more potent inhibitors of TXA$_2$ synthetase. Many of the compounds are also more selective in their action in not inhibiting other antiaggregatory-prostaglandin generating enzymes. The compounds of formula (I) also do not produce the side effects found with imidazole upon in vivo administration. The compounds of formula (I) are further capable of inhibiting platelet aggregation in vivo and also are capable of disaggregating platelet clumps.

Imidazoles of formula (I) and acid addition salts thereof may be made by any method known in the art for the synthesis of compounds of analogous structure. In general these methods preferably comprise (a) linking the imidazole ring to the remainder of the molecule; (b) converting a precursor molecule by elimination of a functional group from the imidazole ring; or (c) formation of the desired compound from a corresponding pyrazole, imidazoline, or other unsaturated analogue.

A most convenient method of synthesis involves the reaction of imidazole (formula II) or a salt thereof with an agent of formula (III):

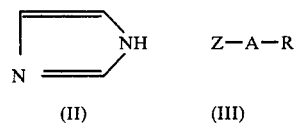

(II)          (III)

wherein R and A are as defined in formula (I) and Z is a leaving group. This reaction is well established in the literature, and the leaving group may be chosen from a variety of substituents but especially halo, preferably chloro or bromo, or from p-toluenesulphonyloxy, but other arylsulphonyloxy, alkanesulphonyloxy or arylalkylsulphonyloxy radicals may be used. The reaction is preferably preformed in the presence of an acid acceptor, for example an alkali metal alkoxide, such as sodium methoxide or potassium tertiary butoxide in the presence of an alkanol. When Z is halo, the reaction may be carried out in the presence of a copper catalyst, e.g, as in an Ullmann reaction, especially when A is a chemical bond. The leaving group Z may itself be formed in situ from the corresponding alkanol (Z=OH) by reaction with a hydrohalogenic acid (e.g. hydrochloric acid or a Lewis acid, such as aluminium chloride: see Japanese Patent Kokai No. 131577/77) and the resulting agent of formula (III) reacted directly with imidazole without prior isolation. Alternatively an alkanol (Z=OH) or a derivative thereof (e.g. Z=R—A—O—) may be reacted directly with imidazole (II) by heating in the presence of a dehydrating agent such as phosphoric acid, or a phosphate (see Japanese Pat. No. 51 105 060), sulphuric acid or sulphates (see Japanese Pat. No. 51 105 061).

Among precursor molecules which may be converted to a compound of formula (I) or an acid addition salt thereof, are substituted imidazole derivatives of formula (IV), or addition salts thereof:

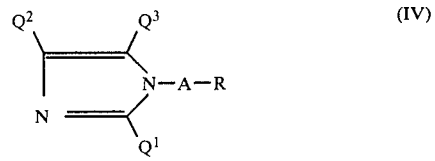

wherein A and R are as defined in formula (I) and $Q^1$, $Q^2$ and $Q^3$ are the same or different, at least one being a radical capable of removal by, for example, reduction or oxidation, the remaining radical or radicals being selected from hydrogen or a radical capable of removal in the same or another manner (e.g. a carboxyl group—see formula (V)—removed by decarboxylation). $Q^1$, $Q^2$ and $Q^3$ may be selected for example from thio (—SH), alkyl-thio (S-alkyl, wherein alkyl has from 1 to 4 carbon atoms) or halo preferably chloro or bromo. The reaction conditions are chosen according to the nature of the radicals $Q^1, Q^2$ and $Q^3$. Desulphurisation may be performed by oxidative or reductive procedures using, for example, nitric acid or Raney nickel; and reductive dehalogenation by the use of zinc and acetic acid or Raney nickel or other reagents known in the art or described in the literature.

Another class of examples include carboxyimidazoles or derivatives thereof of formula (V):

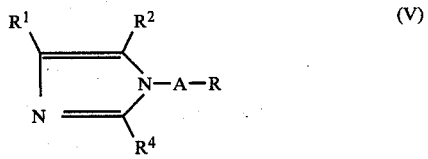

wherein A and R are as defined for formula (I), at least one of $R^1$, $R^2$ and $R^4$ is carboxyl or a derivative thereof (for example an ester such as an alkyl ester, an acid halide such as the chloride, or the nitrile) and the remainder is or are hydrogen or carboxyl or a derivative as described, which may be converted into the imidazoles of formula (I) by any suitable decarboxylation conditions which may simply comprise heating the compounds with or without a catalyst such as copper.

The imidazoles of formula (I) may also be made from a compound of formula (VI):

wherein

is 1-imidazoline, 1-imidazole or 1-pyrazole, $A^1$ is a straight or branched, saturated or unsaturated, radical (which may include a keto group) convertible into (another) group A in formula (I) and $R^3$ is a group convertible to a group R (or another group R) as defined in formula (I) provided that at least one of

$A^1$ and $R^3$ is other than 1-imidazole, a group A and a group R of the product of formula (I). Thus an imidazoline (VII):

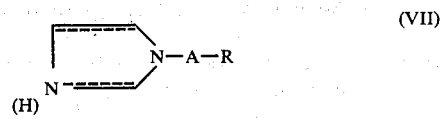

wherein one of ------ represents an extra bond, and A and R are as defined in formula (I) may be dehydrogenated to the corresponding imidazole in the presence of a catalyst, for example by heating to 250° C. in the presence of palladium, nickel or platinum under pressure, or by heating with a dehydrogenating agent, such as selenium or copper oxide. 1-Pyrazole compounds (VI) may be treated with ultra-violet radiation, optionally under an inert atmosphere (e.g. argon) in for example 1,2-dimethoxyethane at room or elevated temperature (see for example "Ring Transformations of Heterocycles" edited van der Plas, Academic Press, 1973 at page 261). The unsaturated imidazoles of formula (I) (in formula (VI), $A^1$ and/or unsaturated $R^3$) may be reduced to the corresponding less saturated or completely saturated compounds with a noble metal catalyst, for example platinum or palladium in an alkanol.

A compound of for example formula (VIII)

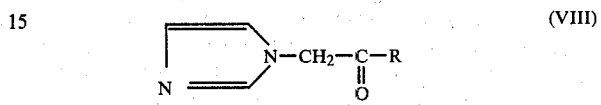

where R is as defined in formula (I), may be reduced at the keto group to a —CH$_2$-group, for example by a Clemmensen reduction.

Compounds of formula (I) may also be prepared by cyclising, preferably in the presence of an acid acceptor, a compound of formula (IX):

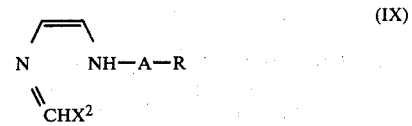

wherein A and R are as defined for formula (I) and $X^2$ is a leaving group, for example as defined for Z in formula (III) above.

Compounds of formula (I) may also be prepared by reacting compound of formula (X):

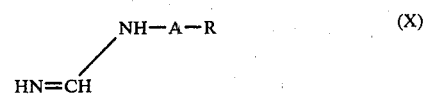

wherein A and R are as defined for formula (I) with a compound of formula (XI)

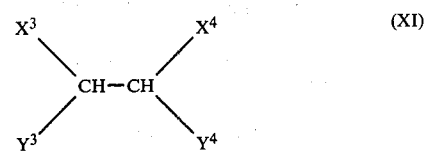

wherein either of $X^3$ and $Y^3$ is a leaving group, such as halo or hydroxy, and the other is hydrogen, or $X^3$ and $Y^3$ are both halo or, together with the CH group to which they are attached, form an aldehyde group or an acetal derivative thereof, e.g both $X^3$ and $Y^3$ are alkoxy; and $X^4$ and $Y^4$ are as defined for $X^3$ and $Y^3$, although they may be the same as or different from $X^3$ and $Y^3$.

An imine salt of for example formula:

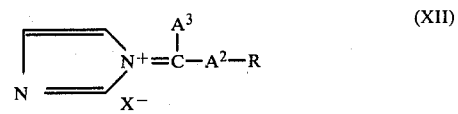

(wherein R is as defined for formula (I) X⁻ is an anion, A² is a chemical bond or a straight or branching, saturated or unsaturated acyclic radical, which may include a keto group, A³ is hydrogen or a saturated or unsaturated acyclic radical, which may include a keto group, with the proviso that A² and A³ together contain no more than 5 carbon and hetero atoms), may be reduced to the corresponding compound of formula (I) by, e.g., zinc and a mineral acid, e.g. hydrochloric acid.

When R in formula (I) is substituted by hydroxy or halo, the substituents may be introduced by reaction of carbon to carbon double or triple bonds in an intermediate unsaturated compound with a suitable electrophilic reagent capable of adding across the double or triple bonds to provide the substituents in the group R. For example a di-bromo-substituted R group can be made by brominating a compound in which the group R contains a double bond with a solution of bromine in an organic solvent such as chloroform. A di-hydroxy-substituted R group may be prepared by oxidising a compound in which the group R contains a double bond with, for example, peracetic acid or with osmium tetroxide and hydrogen peroxide.

These hydroxylation reactions may also be used to introduce hydroxyl groups into the group A, if desired, using as intermediates compounds of formula (I) in which A is unsaturated.

When the group R contains a nitrogen atom to which the A group is attached, the compound of formula (I) may be prepared by a Mannich reaction reacting imidazole (II) with the parent hetero-R compound containing an —NH— group and an aldehyde (to form the linking group A) which may have up to 6 carbon or hetero atoms. In this Mannich reaction the imidazole and hetero-R group will in the product be attached to the same carbon atom of A.

Preferably the reaction between the hetero-R compound and the aldehyde, preferably formaldehyde, is carried out before the reaction with the imidazole, the reaction with the imidazole preferably being carried out in acidic solution.

Compounds of formula (I) in which R contains a ring nitrogen atom to which the group A is attached may also be prepared by reaction of imidazole with an intermediate Mannich base. The intermediate Mannich base may be prepared by reaction of the parent heterocyclyl compound containing a ring —NH— group and an aldehyde containing up to 6 carbon (and hetero) atoms with a cyclic or acyclic secondary amine. Alternatively, if the intermediate base is prepared by reacting imidazole with an aldehyde as just defined and a cyclic or acyclic secondary amine (other than the parent heterocyclyl compound RH), the desired heterocyclyl group R may be introduced by reaction of the RH compound with the intermediate Mannich base.

The intermediates for use in the above described reactions may also be made by conventional methods known in the art. Thus the 1-pyrazole and 1-imidazoline intermediates (formula (VI)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), Z=OH) where, in such compounds, R contains a carbon to carbon double bond the alcohol is conveniently prepared by the Prins reaction from paraformaldehyde and the corresponding unsaturated compound containing one less carbon atom (cf. *Bull. Chem. Soc.* Japan 46/48, 2512-5 1973). Similarly when A is unsaturated with from 3 to 6 carbon (or hetero) atoms, the alcohol may be prepared from paraformaldehyde and the corresponding unsaturated A compound with 2 to 5 carbon (or hetero) atoms. The substituted imidazole intermediates of formula (IV) may be made in known manner, for example see "Imidazole and its derivatives" Part 1, Ed. K. Hoffmann, Inter-science Publishers Inc. New York, 1973. For example the 2-thioimidazoles of formula (IV) may be made by cyclisation with thiocyanate, of an acetal of formula (XIII):

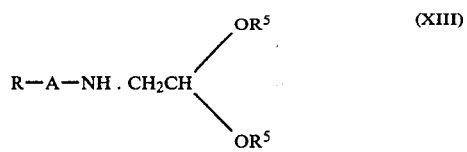

wherein R⁵ is alkyl, aryl or arylalkyl.

The pharmaceutically acceptable acid addition salts of the compounds of formula (I) may be prepared by any method known in the art. In particular they may be prepared by treating the parent imidazole with the appropriate acid or by anion-exchange. Examples of the addition salts of the compounds of formula (I) include those salts derived from the following acids: oxalic, hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic.

The imidazoles of formula (I) may be used in conjunction with a phosphodiesterase inhibitor, which provides a further, synergistic, increase in effect, as it acts against platelet aggregation by a different pathway.

Suitable phosphodiesterase inhibitors for use in potentiating the anti-aggregatory effects of the active compounds include as such or as pharmaceutically acceptable salts:

(a) Xanthine derivatives such as:
Theophylline (3,7-dihydro-1,3-dimethyl-1H-purine-2,6-dione);
Caffeine (3,7-dihydro-1,3,7-trimethyl-1H-purine-2,6-dione); and
Aminophylline (adduct of Theophylline and 1,2-ethanediamine (2:1)).

(b) Isoquinoline derivatives, for example:
Papaverine (1-[(3,4-dimethoxyphenyl)methyl]-6,7-dimethoxyisoquinoline);

(c) Derivatives of pyrimido[5,4-d]-pyrimidine, for example:
Dipyridamole (2,2',2'',2'''-(4,8-dipiperidinopyrimido[5,4-d]pyrimidin-2,6-diyldinitrilo)tetraethanol) and its salts;

(d) Derivatives of thieno[3,2-d]pyrimidine, for example:
N-[4-(4-morpholinyl)thieno[3,2-d]pyrimidin-2-yl]-1,2-ethanediamine.

(e) Derivatives of pyrazolo[3',4':2,3]pyrido-[4,5-b]-[1,5]benzodiazepin-6-(3H)one, for example:
3-Ethyl-7,12-dihydro-7,12-dimethylpyrazolo-[4',3':5,6]pyrido[4,3-b]-[1,5]benzodiazepin-6-(3H)-one;

(f) Derivatives of 1H- or 2H-pyrazolo[3,4-b]pyridine, for example:

4-(Butylamino)-1-ethyl-1H-pyrazolo[3,4-b]-pyridine-5-carboxylic acid ethyl ester; and 2-Methyl-6-phenyl-4-(1-piperidinyl)-2H-pyrazolo-[3,4-b]pyridine;

(g) Derivatives of 5H-furo-[3,4-e]pyrazolo-[3,4-b]pyridine-5-one, for example:

4-(Butylamino)-1-ethyl-1,7-dihydro-7-hydroxy-5H-furo-[3,4-e]pyrazolo[3,4-b]pyridine-5-one; and (h) Derivatives of 1-(2H)-naphthalenone, for example:

2-(Dimethylamino)methyl-3,4-dihydro-7-methoxy-1(2H)-naphthalenone

The active compounds are particularly useful in the treatment and/or prophylaxis of thromboembolic disorders in mammals, including man. It is to be understood that the term "thrombo-embolic disorders" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. They may also be used in laboratory animals, e.g. cats, dogs, rabbits, monkeys and rats, for these purposes, in order to develop new methods and techniques for organ and limb transplants.

The active compounds may also exhibit some vasodilatory action on blood vessels and therefore have a utility as anti-hypertensives for the treatment of high blood pressure in mammals, including man.

The active compounds may also be used in the preventing treatment or prophylaxis of angina pectoris and in the prevention or delay of the onset of shock.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 8 mg per kg. A suitable single oral dose for an adult human lies within the range of 50 to 1800 mg, preferably 200 to 900 mg, especially 300 to 700 mg, for example 550 mg, given say three times a day.

While it is possible for an active compound to be administered as the pure chemical, it is preferable to present it as a pharmaceutical formulation. The formulations, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formulation and not being deleterious to the recipient thereof. Unit doses of a formulation may contain between 60 mg and 1.5 g of an active compound.

The formulations include those suitable for oral, rectal, vaginal or parenteral (including subcutaneous, intramuscular and intravenous) administration. Preferred formulations include tablets, capsules, elixirs and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier which constitutes one or more accessary ingredients. In general the formulations are prepared by uniformly and intimately bringing into association the active compound with liquid carriers or finely divided solid carriers or both, and then, if necessary, shaping the product into the desired formulation.

It will be appreciated from the foregoing that the present invention may provide at least the following features:

(a) Novel 1-substituted imidazoles of formula (I) and acid addition salts thereof.

(b) Methods of preparing the imidazoles of formula (I) and acid addition salts thereof.

(c) Pharmaceutical formulations containing the imidazoles of formula (I) or a pharmaceutically acceptable acid addition salt thereof together with a pharmaceutically acceptable carrier.

(d) Methods of preparing the pharmaceutical formulations containing the imidazoles of formula (I) or a pharmaceutically acceptable acid addition salt thereof.

(e) A method for the treatment or prophylaxis of a thrombo-embolic disorder in a mammal or mammalian tissue, including man or human tissue, comprising administering an active compound.

(f) An 1-substituted imidazole of formula (I) or salt thereof as an active agent for the treatment of a thrombo-embolic disorder in a mammal or mammalian tissue, including man or human tissue.

The following Examples are provided by way of an illustration of the present invention and should in no way be construed as constituting a limitation thereof. All temperatures are given in degrees Celsius.

EXAMPLE 1

Preparation of
1[2-(Adamantan-1-yl)-2-oxoethyl]imidazole

A mixture of adamantan-1-yl bromomethyl ketone (6.43 g, 0.025 mol), imidazole (1.7 g, 0.025 mol) and potassium tert-butoxide (2.81 g, 0.025 mol) in dry butan-1-ol (30 ml) was stirred and heated under reflux for 8 h.

After cooling, the reaction mixture was filtered, and the filtrate was concentrated under reduced pressure, to afford an oil which solidified on standing. The solid was dissolved in hydrochloric acid (75 ml) and the acid solution was washed with ether (1×100 ml). The acid solution was then basified with sodium hydroxide solution (10 M), and the basic solution was then extracted with chloroform (3×100 ml). The chloroform extracts were combined and dried (MgSO$_4$), when evaporation of the chloroform under reduced pressure gave a solid which was purified using a silica gel column and by elution with chloroform/methanol (9:1). The product fractions were combined and concentrated to afford a solid which was purified by crystallisation from ethyl acetate, to afford 1-[2-(Adamantan-1-yl)-2-oxoethyl]imidazole, m.p. 130°–130.5°.

EXAMPLE 2

1-[2-(Adamantan-1-yl-2-hydroxyethyl]imidazole

A solution of 1-[2-(adamantan-1-yl)-2-oxoethyl-]imidazole (4.57 g, 18.7 mmol) in dry tetrahydrofuran (20 ml) was added dropwise to a stirred, cooled suspension of lithium aluminium hydride (0.76 g, 0.02 mol) in dry tetrahydrofuran, under dry nitrogen, at such a rate that the reaction temperature did not exceed 10°.

Following the addition, the reaction mixture was stirred for 0.5 h, when water (20 ml) was added. The reaction mixture was filtered, and the residue was washed with tetrahydrofuran (100 ml). The tetrahydrofuran solutions were combined and dried ($MgSO_4$), and the solution was then concentrated under reduced pressure to afford a brown solid. Recrystallisation of the solid from ethyl acetate/ethyl alcohol gave 1-[2-(adamantan-1-yl)-2-hydroxyethyl]imidazole, m.p. 236°.

EXAMPLE 3

(a) Preparation of 2-(6,6-Dimethylbicyclo[3.1.1]heptan-2-yl)ethan-1-ol

This compound was prepared according to the method of R. Baronnet et al., Eur. J. Med. Chem., 1974, 9 No. 2, 182.

(b) Preparation of 1-Bromo-2-(6,6-dimethylbicyclo[3.1.1.]heptan-2-yl)ethane

This compound was also prepared according to the method of R. Baronnet et al., Eur. J. Med. Chem., 1974, 9 No. 2, 182.

(c) Preparation of 1-[2-(6,6-dimethylbicyclo[3.1.1.]heptan-2-yl)ethyl-]imidazole 1-Bromo-2-(6,6-dimethylbicyclo[3.1.1.]heptan-2-yl)ethane (9.24 g, 0.04 mol) was added dropwise to a stirred solution of potassium tert-butoxide (4.48 g, 0.04 mol) and imidazole (2.72 g, 0.04 mol) in dry butan-1-ol (100 ml). Following the addition, the reaction mixture mixture was stirred and heated under reflux for 6 h.

After cooling, the reaction mixture was filtered, and the filtrate was concentrated under reduced pressure. The residue was suspended in hydrochloric acid (150 ml, 2 M), and the acid solution was washed with ether (70 ml). The acid solution was then basified with sodium hydroxide solution, and the basic solution was extracted with chloroform (3×50 ml). The combined chloroform extracts were dried ($MgSO_4$), and the chloroform was then removed under reduced pressure to afford a yellow oil.

A 6.0 g sample of the crude oil was purified using a silica gel column and by elution with chloroform/methanol (9:1). The product fractions were pooled and concentrated to give a yellow oil. Distillation of the oil gave 1-[2-(6,6-dimethylbicyclo[3.1.1.]heptan-2-yl)ethyl-]imidazole as a colourless oil, b.p. 117°/0.2 mm Hg.

EXAMPLE 4

Preparation of 1-Bromo-2-(6,6-dimethylbicyclo[3.1.1.]hept-2-en-2-yl)ethane

A solution of 2-(6,6-dimethylbicyclo[3.1.1.]hept-2-en-2-yl)-ethan-1-ol (16.6 g, 0.1 mol) in light petroleum (60 ml) was stirred and cooled to −10° when a solution of phosphorus tribromide (14.08 g, 0.052 mol) in light petroleum (25 ml) was added dropwise at −10°. Following the addition, the reaction mixture was stirred and maintained at −10° for 1 h. and was then allowed to reach ambient temperature. The reaction mixture was then poured into water (250 ml), and the organic layer was separated. The aqueous layer was extracted with light petroleum (3×50 ml) when the organic layer and light petroleum extracts were combined and washed with sodium hydroxide solution (1×250 ml, 2 M) and with water (1×250 ml). The light petroleum solution was then dried ($MgSO_4$), and the solution was concentrated under reduced pressure to give a yellow oil. The oil was purified using a silica gel column and by elution with chloroform. The product fractions were combined and concentrated to afford an oil which was distilled, to give 1-bromo-2-(6,6-dimethylbicyclo[3.1.1.]hept-2-en-2-yl)ethane, b.p. 51°–54°/0.275 mm Hg.

Preparation of 1-[2-(6,6-Dimethylbicyclo[3.1.1.]hept-2-en-2-yl)ethyl-]imidazole A mixture of potassium tert-butoxide (0.49 g, 4.4 mmol) and imidazole (0.3 g, 4.4 mmol) in dry butan-1-ol (30 ml) was stirred and heated under reflux when 1-bromo-2-(6,6-dimethylbicyclo[3.1.1.]hept-2-en-2-yl)ethane (0.73 g, 3.2 mmol) was added dropwise. Following the addition, the reaction mixture was stirred and heated under reflux for 4 h.

After cooling, the reaction mixture was filtered, and the filtrate was concentrated under reduced pressure. The residue was suspended in hydrochloric acid (50 ml, 2 M), and the acid solution was washed with ether (1×25 ml). The acid solution was then basified with sodium hydroxide solution (10 M), and the basic mixture was extracted with chloroform (3×25 ml). The chloroform solutions were combined and dried ($MgSO_4$). Concentration of the solution gave a brown oil which was purified using a silica gel column and by elution with chloroform/methanol (9:1). The product fractions were pooled and concentrated to give an oil. Distillation of the oil gave 1-[2-(6,6-dimethylbicyclo[3.1.1.]hept-2-en-2-yl)ethyl]imidazole, b.p. 91°–92°/0.03 mm Hg.

EXAMPLE 5

(a) Preparation of Bicyclo[2.2.1]hept-5-ene-2-methanol

A solution of sodium borohydride (15.49 g, 0.409 mol) in absolute ethanol (350 ml) was added dropmise to a stirred solution of bicyclo[2.2.1]hept-5-ene-2-carboxaldehyde (50.0 g, 0.409 mol) in absolute ethanol (300 ml) at 50°–60°. Following the addition, the reaction mixture was stirred at ambient temperature for 4 h. The solution was then acidified to congo red with dilute hydrochloric acid (2 M), filtered, and this solution was reduced to low volume under reduced pressure. Water (200 ml) was then added, and the mixture was stirred, when a white solid seperated. The reaction mixture was filtered, and the agueous solution was then extracted with ether (3×150 ml). The ether extracts were combined and dried ($MgSO_4$), and the solution was then concentrated under reduced pressure to afford a pale yellow oil. Distillation of the oil gave bicyclo[2.2.1-]hept-5-ene-2-methanol, b.p. 98°–100°/15 mm Hg.

(b) Preparation of 5-Chloromethylbicyclo[2.2.1]hept-2-ene

A mixture of triphenylphosphine (20.98 g, 0.08 mol) and bicyclo[2.2.1]hept-5-ene-2-methanol (5.0 g, 0.0403 mol) in dry carbon tetrachloride (31.5 ml) was stirred and heated at 60° for 6 h. After cooling, the reaction mixture was filtered, and the filtrate was evaporated under reduced pressure to afford a semi-crystalline mass, which was triturated with n-pentane (100 ml). The reaction mixture was filtered, and the filtrate was concentrated under reduced pressure to afford a yellow oil. Distillation of the oil afforded 5-chloromethylbicyclo[2.2.1]hept-2-ene as a colourless oil, b.p. 70°–72°/24 mm Hg.

(c) Preparation of 1-(Bicyclo[2.2.1]hept-5-en-2-ylmethyl)imidazole

A mixture of imidazole (6.94 g, 0.102 mol), potassium tert-butoxide (11.45 g, 0.102 mol) and 5-chloromethylbicyclo[2.2.1]hept-2-ene (14.52 g, 0.102 mol) in dry butan-1-ol (150 ml) was stirred and heated under reflux under dry nitrogen for 45 h.

After cooling, the reaction mixture was concentrated under reduced pressure to afford as brown oil, which was dissolved in dilute hydrochloric acid (2 M). The acid solution was washed with ether (150 ml), and the acid solution was then basified with sodium hydroxide solution (10 M). The basic solution was then extracted with chloroform (3×100 ml), and the chloroform extracts were then combined and dried (MgSO$_4$). The chloroform solution was then concentrated under reduced pressure, to afford an oil which was chromatographed on silica gel, using chloroform/methanol (9:1) as eluent. The product fractions were combined and concentrated under reduced pressure to afford a colourless oil. Distillation of the oil afforded 1-(bicyclo[2.2.1]hept-5-en-2-ylmethyl)imidazole, b.p. 90°–94°/0.01 mm Hg.

EXAMPLE 6

Preparation of 1-(Bicyclo[2.2.1]heptan-2-ylmethyl)imidazole

A mixture of 1-(bicyclo[2.2.1]hept-5-en-2-ylmethyl)imidazole (2.0 g, 11.48 mmol) and palladium on charcoal (0.2 g, 10%) in dry ethanol was shaken in an atmosphere of hydrogen for 4.5 h. The reaction mixture was then filtered through Hyflo-Supercel, and the filtrate was concentrated under reduced pressure to afford a colourless oil. Distillation of the oil afforded 1-(bicyclo[2.2.1]heptan-2-ylmethyl)imidazole as a colourless oil, b.p. 82°–84°/0.15 mm Hg.

EXAMPLE 7

Preparation of Salts of 1-[2-(1-Adamantanyl)ethyl]imidazole (a) Hydrogen Fumarate A solution of fumaric acid (0.5 g, 4.31 mmol) in boiling ethanol (15 ml) was added to a solution of 1-[2-(1-Adamantyl)ethyl]imidazole (1.0 g, 4.34 mmol) in hot ethanol (10 ml). After boiling for 0.15 h, the mixture was concentrated to afford a white solid. Recrystallisation of the solid from ethyl acetate gave 1-[2-(1-adamantyl)ethyl]imidazole hydrogen fumarate as a colourless solid, m.p. 117°–118°.

(b) Hydrogen Oxalate

A solution of oxalic acid (0.18 g, 2.0 mmol) in boiling ethanol (10 ml) was added to a hot solution of 1-[2-(1-adamantyl)ethyl]imidazole (0.5 g, 2.17 mmol). After boiling for 0.15 h, the reaction mixture was concentrated under reduced pressure to afford a white solid. Recrystallisation of the solid from propan-2-ol gave 1-[2-(1-adamantanyl)ethyl]imidazole hydrogen oxalate, m.p. 182°–183°.

EXAMPLE 8

Preparation of Salts of 1-[2-(6,6-dimethylbicyclo[3.1.1]heptan-2-yl)ethyl]imidazole (a) Hydrogen Fumarate A solution of 1-[2-(6,6-dimethylbicyclo[3.1.1]heptan-2-yl)ethyl]imidazole (0.8 g, 3.67 mmol) in hot ethanol (20 ml) was added to a solution of fumaric acid (0.39 g, 3.36 mmol) in hot ethanol (20 ml). After boiling for 0.15 h, the mixture was concentrated to afford a white solid. Recrystallisation of the solid from ethyl acetate afforded 1-[2-(6,6-dimethylbicyclo[3.1.1]heptan-2-yl)ethyl]imidazole hydrogen fumarate, m.p. 100°–102°.

(b) Hydrogen Oxalate

A solution of 1-[2-(6,6-dimethylbicyclo[3.1.1]heptan-2-yl)ethyl]imidazole (0.8 g, 3.67 mmol) hot ethanol (10 ml) was added to a solution of oxalic acid (0.3 g, 3.33 mmol) in hot ethanol (20 ml). After boiling the reaction mixture for 0.15 h, the solution was concentrated under reduced pressure to afford a white solid. Recrystallisation of the solid from propan-2-ol gave 1-[2-(6,6-dimethylbicyclo[3.1.1]heptan-2-yl)ethyl]imidazole hydrogen oxalate, m.p. 172°–174°.

(c) Hydrogen Succinate

A solution of 1-[2-(6,6-dimethylbicyclo[3.1.1]heptan-2-yl)ethyl]imidazole (0.8 g, 3.67 mmol) in hot ethanol (10 ml) was added to a solution of succinic acid (0.4 g, 3.39 mmol) in hot ethanol. After boiling for 0.15 h, the reaction mixture was concentrated to afford a colourless oil which solidified on trituration with ethyl acetate/petroleum ether (b.p. 40°–60°) to a white solid. Recrystallisation of the solid from ethyl acetate/petroleum ether (b.p. 40°–60°) afforded 1-[2-(6,6-dimethylbicyclo[3.1.1]heptan-2-yl)ethyl]imidazole hydrogen succinate.

EXAMPLE 9

(a) Preparation of 2-Chloromethyl-6,6-dimethylbicyclo-[3.1.]hept-2-ene

A mixture of triphenylphosphine (7.87 g, 0.03 mol) and 6,6-dimethylbicyclo[3.1.1]hept-2-ene-2-methanol (3.04 g, 0.02 mol) in dry carbon tetrachloride (14.0 ml) was stirred and heated at 60° for 4.0 h. After cooling, the reaction mixture was filtered, and the filtrate was concentrated under reduced pressure to afford a semi crystalline mass. This residue was triturated with n-pentane (30 ml), and the mixture was filtered. The filtrate was concentrated under reduced pressure, and the resulting oil was distilled, to afford 2-chloromethyl-6,6-dimethylbicyclo[3.1.1]hept-2-ene as a colourless oil, b.p. 32°–33°/0.2 mm Hg.

(b) Preparation of 1-(6,6-Dimethylbicyclo[3.1.1]hept-2-en-2-ylmethyl)imidazole

A mixture of potassium tert-butoxide (1.06 g, 9.4 mmol), imidazole (0.64 g, 9.4 mmol), and 2-chloromethyl-6,6-dimethylbicyclo[3.1.1]hept-2-ene (1.6 g, 9.4 mmol) in dry butan-1-ol (25 ml) was stirred and heated under reflux for 1.5 h.

After cooling, the reaction mixture was filtered and the filtrate was concentrated under reduced pressure. The residue was taken up in dilute hydrochloric acid (100 ml, 2 M), and the acid solution was washed with ether (75 ml). The acid solution was then basified with sodium hydroxide solution (10 M), and the basic solution was then extracted with chloroform (3×50 ml). The chloroform extracts were combined, dried, (MgSO$_4$), and then concentrated under reduced pressure to afford a brown oil. The oil was chromatographed using a silica gel column and by elution with chloroform/methanol (9:1). The product fractions were pooled and concentrated to afford an oil, which was distilled, to give 1-(6,6-dimethylbicyclo[3.1.1]hept-2-en-2-ylmethyl)imidazole, b.p. 98°/0.1 mm Hg.

EXAMPLE 10

Preparation of
1-(6,6-Dimethylbicyclo[3.1.1]heptan-2-yl-methyl)imidazole

A mixture of 1-(6,6-dimethylbicyclo[3.1.1]hept-2-en-2-ylmethyl)imidazole (0.75 g, 3.7 mmol) and palladium on charcoal (0.075 g, 10%) in dry ethanol (40 ml) was shaken in an atmosphere of hydrogen at 40° for 7 h. After cooling, the reaction mixture was filtered through hyflo-supercel, and the filtrate was concentrated under reduced pressure to afford a colourless oil, which was distilled to give 1-(6,6-dimethylbicyclo[3.1.1]heptan-2-ylmethylimidazole, b.p. 100/102°/0.15 mm Hg.

EXAMPLE 11

(a) Preparation of 1-(Adamantan-1-yl)-2-bromoethane

A mixture of hydrobromic acid (26.2 g, 48%), concentrated sulphuric acid (10.82 g), and 2-(adamantan-1-yl)ethanol (10.82 g, 0.06 mol) was stirred and heated under reflux for 6 h. After cooling, water (60 ml) was added to the reaction mixture and the mixture was shaken. The organic layer was separated, and was then extracted with ether (3×100 ml). The extracts were combined, washed with water (1×20 ml) and with sodium carbonate solution (20 ml, 10% w/v) and the ether solution was then dried (MgSO$_4$). The ether solution was concentrated under reduced pressure to give a solid, which was recrystallised from aqueous ethanol, to afford 1-(adamantan-1-yl)-2-bromoethane as white plates, m.p. 71°–72°.

(b) Preparation of
1-[2-(Adamantan-1-yl)ethyl]imidazole

A mixture of imidazole (1.09 g, 16.03 mmol), 1-(adamantan-1-yl)-2-bromoethane (3.90 g, 15.99 mmol) and potassium tert-butoxide (1.8 g, 16.0 mmol) in dry butan-1-ol (50 ml) was stirred and heated under reflux for 9.5 h.

After cooling, the reaction mixture was filtered and the filtrate was concentrated under reduced pressure to give a brown oil, which was taken up in dilute hydrochloric acid (2 M) and the acid solution was then washed with ether (75 ml). The acid solution was then basified with sodium hydroxide solution (10 M), and the basic solution was extracted with chloroform (3×100 ml). The chloroform solutions were combined, dried (MgSO$_4$), and the chloroform was then removed under reduced pressure to afford an oil, which was chromatographed using silica gel and chloroform/methanol (9:1) as eluent. The product fractions were combined and concentrated under reduced pressure to afford an oil. The oil was distilled to give the product b.p. 150°–160°/1.0 mm Hg which solidified on cooling. Recrystallisation of the solid from petroleum ether (b.p. 40°–60°) gave 1-[2-(adamantan-1-yl)ethyl]imidazole as colourless plates, m.p. 64°–65°.

EXAMPLE 12

(a) Preparation of
2-Chloromethyl-1,4-dioxaspiro[4.5]decane

A mixture of cyclohexanone (108.0 g, 1.1 mol), 3-chloropropane-1,2-diol (110.5 g, 1.0 mol) and p-toluenesulphonic acid (1.25 g) in benzene (125 ml) was boiled for 3.0 h, and the water formed during the reaction was removed using a Dean and Starke apparatus.

After standing overnight at ambient temperature, the reaction mixture was treated with sodium acetate (1.5 g), and was then filtered. The filtrate was concentrated under reduced pressure to afford a brown oil, which was distilled, giving 2-chloromethyl-1,4-dioxaspiro[4.5]decane as a colourless oil, b.p. 107°–110°/10 mm.

(b) Preparation of
1-(1,4-Dioxaspiro[4.5]decan-2-ylmethyl)imidazole

A mixture of potassium tert-butoxide (11.2 g, 0.1 mol), imidazole (6.8 g, 0.1 mol) and 2-chloromethyl-1,4-dioxaspiro[4.5]decane (19.05 g, 0.1 mol) in dry butan-1-ol (150 ml) was stirred and heated under reflux for 66 h.

After cooling, the reaction mixture was filtered and the filtrate was concentrated under reduced pressure to afford a brown oil. The oil was purified using a silica gel column and by elution with chloroform/methanol (9:1). The product fractions were pooled and concentrated, to give a yellow oil which was distilled, affording 1-(1,4-dioxaspiro[4.5]decan-2-ylmethyl)imidazole, b.p. 120°/0.09 mm.

EXAMPLE 13

(a) Preparation of 2-Chlorobicyclo[2.2.1]heptane

A mixture of triphenylphosphine (52.72 g, 0.2 mol) and exo-2-hydroxybicyclo[2.2.1]heptane (15.0 g, 0.134 mol) in dry carbon tetrachloride (80 ml) was stirred and heated at 60° for 4 hr. After cooling, the reaction mixture was filtered and the filtrate was concentrated under reduced pressure to afford a semi-crystalline residue. The residue was ground with n-pentane (50 ml), and the mixture was filtered. Evaporation of the n-pentane under reduced pressure gave a yellow oil which was distilled, to give 2-chlorobicyclo[2.2.1]heptane as a colourless oil, b.p. 51°–52°/12 mm.

(b) Preparation of
1-(Bicyclo[2.2.1]heptan-2-yl)imidazole

A mixture of potassium tert-butoxide (2.15 g., 0.0192 mol), imidazole (1.31 g, 0.0192 mol) and 2-chlorobicyclo[2.2.1]heptane (2.5 g, 0.0192 mol) in dry butan-1-ol (25 ml.) was stirred and heated under reflux for 48 h.

After cooling, the reaction mixture was filtered, and the filtrate was concentrated under reduced pressure. The residue was dissolved in hydrochloric acid (100 ml, 2 M), and the acid solution was washed with ether (50 ml). The acid solution was then basified with sodium hydroxide solution (10 M), and the basic solution was then extracted with chloroform (3×50 ml). The chloroform extracts were combined and dried (MgSO$_4$), and the chloroform was removed under reduced pressure to afford 1-(bicyclo[2.2.1]heptan-2-yl)imidazole.

EXAMPLE 14

(a) Preparation of 3-cyano-3-hydroxy-1-azabicyclo[2.2.2]octane

A solution of potassium cyanide (10.15 g, 0.156 mol) in water (31.25 ml) was added dropwise to a solution of 1-azabicyclo[2.2.2]-octan-3-one hydrochloride (25.0 g, 0.155 mol) in water (31.25 ml) at 0°–5°. Following the addition, the reaction mixture was stirred for 3 h and then filtered. The solid was washed with ice-cold water (2×15 ml) and was then dried over phosphorus pentoxide overnight, m.p. 155°–156°. Recrystallisation of a 1 g sample from dioxane gave pure 3-cyano-3-hydroxy-1-azabicyclo[2.2.2]octane, m.p. 172°–173°.

(b) Preparation of 3-Hydroxy-3-methoxycarbonyl-1-azabicyclo[2.2.2]octane

Powdered 3-cyano-3-hydroxy-1-azabicyclo[2.2.2]octane (19.81 g, 0.13 mol) was added portionwise to a solution of hydrogen chloride (106 g, 2.9 mol) in dry methanol (200 ml). Following the addition, the reaction mixture was left at ambient temperature for 36 h, and was then stirred and heated under reflux for 3 h.

After cooling, reaction mixture was concentrated under reduced pressure to afford a solid which was dissolved in water (30 ml). The aqueous solution was rendered alkaline with potassium carbonate and the basic solution extracted with chloroform (3×100 ml). The chloroform solutions were combined and dried (MgSO$_4$), and the chloroform was removed under reduced pressure to afford a solid which was recrystallised from n-pentane to give 3-hydroxy-3-methoxycarbonyl-1-azabicyclo[2.2.2]octane, m.p. 122°.

(c) Preparation of 3-Methoxycarbonyl-1-azabicyclo[2.2.2]oct-2-ene hydrochloride

Powdered 3-hydroxy-3-methoxycarbonyl-1-azabicyclo[2.2.2]octane (16.0 g, 0.086 mol) was added protionwise to thionyl chloride (100 ml) at 0°. Following the addition, the reaction mixture was stirred and heated under reflux for 48 h. The thionyl chloride was then removed under reduced pressure to afford a solid, which was recrystallised from acetone, giving 3-methoxycarbonyl-1-azabicyclo[2.2.2]oct-2-ene hydrochloride, m.p. 178°–179°.

(d) Preparation of 3-Methoxycarbonyl-1-azabicyclo[2.2.2]octane hydrochloride

A mixture of 3-methoxycarbonyl-1-azabicyclo[2.2.2]octane hydrochloride (6.4 g, 0.035 mol) and platinum oxide (0.47 g) in dry methanol (75 ml) was stirred under atmosphere of hydrogen until there was no further uptake of hydrogen. The reaction mixture was then filtered through hyflo-supercel and the filtrate was concentrated under reduced pressure to afford a solid which was recrystallised from acetone, to give 3-methoxycarbonyl-1-azabicyclo[2.2.2]octane hydrochloride, m.p. 167°–169°.

(e) Preparation of 3-Hydroxymethyl-1-azabicyclo[2.2.2]octane hydrochloride

3-Methoxycarbonyl-1-azabicyclo[2.2.2]octane hydrochloride (4.0 g; 0.0375 mol) was dissolved in water (20 ml) and sodium carbonate was added portionwise until the solution was alkaline to litmus. The aqueous solution was then extracted with ether (3×100 ml), and the ether solutions were combined, dried (MgSO$_4$) and then concentrated to afford an oil.

The oil was dissolved in ether (50 ml) and was then added dropwise to a stirred suspension of lithium aluminium hydride (1.7 g, 0.045 mol) in dry ether (30 ml), under dry nitrogen. The addition was carried out at such a rate that the temperature of the reaction mixture did not exceed 25°, and following the addition, the reaction mixture was stirred for 2 h. The excess lithium aluminium hydride was destroyed by the careful addition of water (15 ml), and the reaction mixture was then filtered and the solid was washed with ether. The ether solution was dried (MgSO$_4$) and the ether was evaporated to afford the product as a pale yellow oil.

(f) Preparation of 3-Chloromethyl-1-azabicyclo[2.2.2]octane

A mixture of 3-hydroxymethyl-1-azabicyclo[2.2.2]octane (3.0 g; 0.0213 mol), and triphenylphosphine (11.16 g, 0.0426 mol) in dry carbon tetrachloride (10 ml) was stirred and heated at 60° for 5 h. The reaction mixture was filtered, and the filtrate was concentrated under reduced pressure to afford a semi-crystalline mass.

The residue was ground with n-pentane (20 ml), and the triphenylphosphine oxide was filtered off. The filtrate was concentrated under reduced pressure to afford 3-chloromethyl-1-azabicyclo[2.2.2]octane as a pale yellow oil.

(g) Preparation of 1-(1-Azabicyclo[2.2.2]octan-3-ylmethyl)imidazole

A mixture of 3-chloromethyl-1-azabicyclo[2.2.2]octane (2.5 g; 15.6 mmol), imidazole (1.06 g, 15.6 mmol) and potassium tert-butoxide (1.75 g, 15.6 mmol) in dry butan-1-ol (20 ml) was stirred and heated under reflux for 48 h.

After cooling, the reaction mixture was filtered, and the filtrate was evaporated under reduced pressure to afford a brown oil. The oil was suspended in hydrochloric acid (20 ml, 2 M) and the acid solution was washed with ether. The acid solution was then basified with sodium hydroxide solution (2 M) and the basic solution was then extracted with chloroform (3×50 ml). The chloroform solutions were combined, dried (MgSO$_4$), and the chloroform solution was then concentrated under reduced pressure to afford a brown oil. The oil was purified using a silica gel column, and by elution with chloroform/methanol (9:1). The product fractions were pooled and concentrated to afford 1-(1-azabicyclo[2.2.2]octan-3-ylmethyl)imidazole.

EXAMPLE 15

(a) Preparation of 1,2-[Bis-(bicyclo[2.2.1]hept-5-en-2-yl)]ethanol

A Grignard reagent was prepared from 5-chloromethylbicyclo[2.2.1]hept-2-ene (16.6 g, 116.5 mmol) and magnesium (3.00 g, 125 mmol) in dry ether (20 ml).

To the Grignard reagent was added a solution of bicyclo[2.2.1hept-2-ene-5-carboxaldehyde (13.0 g, 106.5 mmol) in dry ether (100 ml) at 0°–5°. Following the addition, the reaction mixture was stirred and heated under reflux under dry nitrogen for 1 h and was then set aside at ambient temperature overnight.

Next day a solution of ammonium chloride (25 g) in water (60 ml) was added dropwise to the reaction mixture, and the resulting mixture was filtered. The solid was washed with ether, and the aqueous layer was then separated and was washed with ether (3×100 ml). The ether solutions were combined, dried (MgSO$_4$) and the ether was then evaporated to afford 1,2-[bis-(bicyclo[2.2.1]hept-5-en-2-yl)]ethanol as a colourless oil.

(b) Preparation of 1,2-[Bis-(bicyclo[2.2.1]hept-5-en-2-yl)]chloroethane

A mixture of 1,2-[bis-(bicyclo[2.2.1hept-5-en-3-yl]ethanol (23.0 g, 0.1 mol) and triphenylphosphine (52.5 g, 0.2 mol) in dry carbon tetrachloride (100 ml) was stirred and heated at 60° for 6 h.

After cooling, the reaction mixture was filtered, and the filtrate was concentrated under reduced pressure to afford a semicrystalline mass. The mass was stirred with n-pentane, and the triphenylphosphine oxide was removed by filtration. The filtrate was concentrated under reduced pressure, to give 1,2-[bis-(bicyclo[2.2.1-]hept-5-en-2-yl)]chloroethane as a colourless oil.

(c) Preparation of 1-{1,2-[Bis-(bicyclo[2.2.1]hept-5-en-2-yl)]ethyl}-imidazole

A mixture of 1,2-[bis-(bicyclo[2.2.1hept-5-en-2-yl)]chloroethane (12.4 g, 0.05 mol), imidazole (3.4 g, 0.05 mol) and potassium tert-butoxide (5.6 g, 0.05 mol) in dry butan-1-ol (50 ml) was stirred and heated under reflux for 48 h.

After cooling, the reaction mixture was filtered, and the filtrate was evaporated under reduced pressure. The residue was suspended in hydrochloric acid (75 ml, 2 M) and the acid solution was washed with ether (1×50 ml). The acid solution was then basified with sodium hydroxide solution, and the basic solution was extracted with chloroform (3×100 ml). The chloroform solutions were combined, dried (MgSO$_4$) and then concentrated to afford a brown oil. The oil was purified on a silica gel column and by elution with chloroform/methanol (9:1); The product fractions were pooled and concentrated, to give 1-{1,2-[bis-(bicyclo[2.2.1]hept-5-en-2-yl)]ethyl}-imidazole as a colourless oil.

EXAMPLE 16

(a) Preparation of 2,3-[Bis-(bicyclo[2.2.1hept-5-en-2-yl)]propan-1-ol

A Grignard reagent was prepared from 1,2-[bis-(bicyclo[2.2.1hept-5-en-yl]ethanol (11.5 g, 0.5 mol) and magnesium (1.5 g, 0.0625 mol) in dry ether (50 ml.). Dry paraformaldehyde (2.0 g) was heated to 190°, and the depolymerised formaldehyde was passed over the vigorously stirred Grignard reagnet using a steady stream of dry nitrogen. Following the addition of the formaldehyde, the reaction mixture was stirred and heated under reflux for 0.5 h. The reaction mixture was then treated with crushed ice (30 g), and then with hydrochloric acid (100 ml, 2 M), and the reaction mixture was then steam distilled.

The ether layer was separated, and the aqueous solution was extracted with ether (3×100 ml). The organic solutions were combined and washed with sodium hydroxide solution (30 ml, 2 M) and then with water (1×35 ml) and was then dried over potassium carbonate. The ether was evaporated under reduced pressure to afford 2,3-[bis-(bicyclo[2.2.1]hept-5-en-2-yl)]propan-1-ol as a colourless oil.

(b) Preparation of 1,2-[Bis-(bicyclo[2.2.1]hept-5-en-2-yl)]-3-chloropropane

This compound was prepared from triphenylphosphine and carbon tetrachloride according to the method described in Example 5.

(c) Preparation of 1-[1,2-Bis(bicyclo[2.2.1]hept-5-en-2-yl)prop-3-yl]imidazole

This compound was prepared from 1,2-[bis-(bicyclo[2.2.1]hept-5-en-2-yl)]-3-chloropropane, potassium tertiary butoxide and imidazole according to the method described in Example 5.

EXAMPLE 17

According to the procedure described in stages (a), (b) and (c) of Example 5, the following compounds may be prepared:
(a) 1-(2-Cyclohexenespirocyclobutan-3'-ylmethyl)imidazole
(b) 1-[2-(3,3-Dimethylbicyclo[2.2.1]heptan-2-ylidene)ethyl]imidazole
(c) 1-(Tricyclo[2.2.1.0$^{3,5}$]heptan-2-ylmethyl)imidazole
(d) 1-Tricyclo[3.2.1.0$^{2,4}$]octan-6-ylmethyl)imidazole
(e) 1-(Adamantan-1-ylmethyl)imidazole
(f) 1-[3-(Adamantan-1-yl)propyl]imidazole
(g) 1-[4-(Adamantan-1-yl)butyl]imidazole
(h) 1[3-(Bicyclo[2.2.1]heptane-2-yl)propyl]imidazole
(i) 1-[2-(Decahydronapth-1-yl)ethyl]imidazole
(j) 1-(Decahydronapth-1-ylmethyl)imidazole

BIOLOGICAL RESULTS EXAMPLE I

Horse platelets were prepared from whole horse blood by differential centrifugation. Approximately 10$^6$ platelets were homogenised in 1 ml 100 mM Tris buffer pH 7.4. Various concentrations of active compound were added and the reaction sets incubated for 5 minutes at ambient temperature. To each tube was added 20 nM of arachidonic acid containing 10$^6$ disintegrations per minute (DPM) of labelled arachidonic acid and the tubes incubated for 3 minutes at 37° C. in a shaking water bath. After incubation the radioactive products were extracted from the acidified aqueous phase with ethyl acetate and after concentration resolved by thin layer chromatography on silica gel with chloroform/methanol/acetic acid/water (90:8:1:0.8) as a developing solvent. The amount of thromboxane produced was measured by scraping the radioactive zone corresponding to thromboxane B$_2$ and estimating the radioactivity in a liquid scintillation counter.

The concentration of active compound to reduce the enzyme activity by 50% (ED$_{50}$) was established. The results are shown in Table A.

The selectivity of the active compounds was measured in a similar manner to that described above and the amount of PGE, PGF and PGD produced was determined. The greater the selectivity, the more of the anti-aggregating prostaglandins are produced.

The ED$_{50}$ and Selectivity results are shown in Table A in which 0 indicates no selectivity; + low selectivity;

++ medium selectivity; +++ high selectivity; ++++ exceptionally high selectivity; ND not determined.

TABLE A

| (Reference compound) | ED$_{50}$ µg/ml | Selectivity |
|---|---|---|
| (Imidazole) | ≧500 | 0 to + |
| (1-Methylimidazole) | ≧200 | ++ |
| 1-[2-(6,6-Dimethylbicyclo[3,1,1]hept-2-en-2-yl)ethyl]imidazole | 4.3 | +++ |
| 1-[2-(6,6-dimethylbicyclo[3.3.1]heptan-2-yl)ethyl]imidazole | 3.5 | +++ |

FORMULATION EXAMPLES

Example A: Tablet formulation

| | |
|---|---|
| Imidazole of formula (I) as a solid or a solid salt thereof | 150 mg |
| Starch | 25 mg |
| Polyvinylpyrrolidone | 2 mg |
| Magnesium stearate | 3 mg |

The imidazole or salt is ground to a fine powder, blended with the starch and then the mixture granulated with an aqueous solution of the polyvinylpyrrolidone. The granules are sieved 1000µ, dried, sieved again and the magnesium stearate added. The mixture is then compressed into tablets.

In this manner, tablets of 1-[2-(6,6-dimethylbicyclo[3,1,1]hept-2-en-2-yl)ethyl]imidazole (as a salt) were prepared.

Example B: Tablet formulation

Tablets (150 mg) of the imidazoles or salts described in the preceding Example are prepared in the same manner from the following ingredients:

| | |
|---|---|
| The Imidazole Compound (as such or as a salt) | 150 mg |
| Lactose | 100 mg |
| Starch | 30 mg |
| Polyvinylpyrrolidone | 2 mg |
| Magnesium stearate | 3 mg |

In the preparation, the lactose is blended with the starch.

Example C: Tablet formulation

Tablets (100 mg) of the imidazoles or salts of Example A are prepared in the same manner from the following ingredients:

| | |
|---|---|
| The Imidazole Compound (as such or as a salt) | 100 mg |
| Sodium starch glycollate | 10 mg |
| Polyvinylpyrrolidone | 2 mg |
| Magnesium stearate | 3 mg |

Example D: Tablet formulation

Tablets (150 mg) of the imidazoles or salts of Example A are prepared in the same manner from the following ingredients, except that the starch, pregelled starch and imidazole compound are all blended together prior to granulation:

| | |
|---|---|
| The Imidazole Compound (as such or as a salt) | 150 mg |
| Starch | 25 mg |
| Pregelled starch | 5 mg |
| Magnesium stearate | 3 mg |

Example E: Injectable formulation

| | |
|---|---|
| Imidazole compound (or salt) of formula (I) | 15.0 g |
| Lactic Acid B.P. | q.s. to pH 3.0 |
| Water for Injections B.P. | to 100.0 ml |

Suspend the compound in ¾ of the available quantity of water. Add sufficient lactic acid to dissolve the compound and to reduce the pH to 3.0 Dilute to volume with Water for Injections.

Sterilise the solution by passage through a membrane filter, pore size 0.22 µm.

Distribute the solution using aseptic precautions into sterilised ampoules, 1 ml per ampoule. Seal by fusion of the glass.

Each 1 ml ampoule supplies 150 mg of the imidazole compound.

Example F: Injectable formulation

| | |
|---|---|
| Imidazole compound or salt of formula (I) | 15.0 g |
| Citric Acid B.P. | q.s. to pH 3.0 |
| Chlorocresol | 0.1 g |
| Water for Injections to | 100.0 ml |

Suspend the compound in ½ the final volume of Water for Injections. Add sufficient citric acid as a 10% solution in Water for Injections to dissolve the compound and reduce the pH to 3.0. Dilute to volume with Water for Injections.

Sterilise the solution by passage through a membrane filter, pore size 0.22 µm.

Distribute the solution with aseptic precautions into sterilised vials, 25 ml per vial. Stopper with sterile rubber closures and seal with an aluminium cap.

Each 1 ml of solution provides 150 mg of the compound.

I claim:

1. 1-[2-(6,6-dimethylbicyclo[3.1.1]hept-2-en-2-yl)ethyl]imidazole or a pharmaceutically acceptable acid addition salt thereof.

2. 1-[2-(adamantan-1-yl)ethyl]imidazole or an acid addition salt thereof.

3. A 1-substituted imidazole selected from
1-[2-(6,6-dimethylbicyclo[3.1.1]heptane-2-yl)ethyl]imidazole;
1-(bicyclo[2.2.1]hept-5-en-2-ylmethyl)imidazole;
1-(bicyclo[2.2.1]heptan-2-ylmethyl)imidazole;
1-(6,6-dimethylbicyclo[3.1.1]heptan-2-ylmethyl)imidazole;
1-(2-cyclo-hexenespirocyclobut-3'-ylmethyl)imidazole;
1-(6,6-dimethylbicyclo[3.1.1]hept-2-en-2-ylmethyl)imidazole;
1-[2-(3,3-dimethylbicyclo[2.2.1]heptan-2-ylidene)ethyl]imidazole;
1-(4-azabicyclo[2.2.2]octan-2-ylmethyl)imidazole; and
1-(8-methyl-8-azabicyclo[3.2.1]octan-3-ylmethyl)imidazole or an acid addition salt thereof.

4. A pharmaceutical composition for use in thromboembolic disorders which comprises a non-toxic medicinally effective amount of a compound or salt of claim 1 in association with a pharmaceutically acceptable carrier.

5. A pharmaceutical composition for use in thromboembolic disorders which comprises a non-toxic medicinally effective amount of a compound or salt of claim 2 in association with a pharmaceutically acceptable carrier.

6. A pharmaceutical composition for use in thromboembolic disorders which comprises a non-toxic medicinally effective amount of a compound or salt of claim 3 in association with a pharmaceutically acceptable carrier.

* * * * *